United States Patent
Neil et al.

(10) Patent No.: US 10,429,296 B2
(45) Date of Patent: Oct. 1, 2019

(54) MULTILAYER FILM METROLOGY USING AN EFFECTIVE MEDIA APPROXIMATION

(71) Applicant: KLA-Tencor Corporation, Milpitas, CA (US)

(72) Inventors: Mark A. Neil, San Jose, CA (US); Mikhail Sushchik, Pleasanton, CA (US); Natalia Malkova, Hayward, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 16/040,798

(22) Filed: Jul. 20, 2018

(65) Prior Publication Data

US 2019/0033211 A1 Jan. 31, 2019

Related U.S. Application Data

(60) Provisional application No. 62/536,880, filed on Jul. 25, 2017.

(51) Int. Cl.
*G01N 21/39* (2006.01)
*G01N 21/956* (2006.01)
(Continued)

(52) U.S. Cl.
CPC .......... *G01N 21/39* (2013.01); *G01B 11/0625* (2013.01); *G01B 11/0641* (2013.01);
(Continued)

(58) Field of Classification Search
CPC ............ G01B 11/0641; G01B 2210/56; G01B 11/0625; G01N 21/211; G01N 21/39;
(Continued)

(56) References Cited

U.S. PATENT DOCUMENTS

| 5,608,526 A | 3/1997 | Piwonka-Corle et al. |
| 5,859,424 A | 1/1999 | Norton et al. |

(Continued)

FOREIGN PATENT DOCUMENTS

| WO | 2014062972 A1 | 4/2014 |
| WO | 2014066679 A1 | 5/2014 |

(Continued)

OTHER PUBLICATIONS

International Search Report and Written Opinion dated Nov. 29, 2018 for PCT/US2018/043582.
(Continued)

*Primary Examiner* — Tri T Ton
(74) *Attorney, Agent, or Firm* — Suiter Swantz pc llo

(57) ABSTRACT

A metrology system includes a controller coupled to a detector to generate a detection signal based on the reflection of an illumination beam from a multilayer film stack. The multilayer film stack may include one or more zones with a repeating pattern of two or more materials. The controller may generate a model of reflection of the illumination beam by modeling the zones as thick films having zone thicknesses and effective permittivity values using an effective medium model relating the effective permittivity values of the zones to permittivity values and volume fractions of constituent materials. The controller may further determine values of the zone thicknesses and the volume fractions using a regression of the detection signal based on the effective medium model and further determine average thickness values of the constituent materials based on the number of films, the zone thicknesses, the volume fractions, and the effective permittivity values.

23 Claims, 10 Drawing Sheets

(51) Int. Cl.
  *G01N 21/47* (2006.01)
  *G02B 27/58* (2006.01)
  *G01N 21/21* (2006.01)
  *G01B 11/06* (2006.01)
(52) U.S. Cl.
  CPC ....... *G01N 21/211* (2013.01); *G01N 21/4788* (2013.01); *G01N 21/95623* (2013.01); *G02B 27/58* (2013.01); *G01B 2210/56* (2013.01); *G01N 2201/068* (2013.01)
(58) Field of Classification Search
  CPC ......... G01N 21/4788; G01N 21/95623; G01N 2201/068; G02B 27/58
  USPC .................................................. 356/625–640
  See application file for complete search history.

(56) References Cited

U.S. PATENT DOCUMENTS

| | | | |
|---|---|---|---|
| 6,429,943 B1 | 8/2002 | Opsal et al. | |
| 7,362,435 B1 | 4/2008 | Johs et al. | |
| 7,478,019 B2 | 1/2009 | Zangooie et al. | |
| 7,933,026 B2 | 4/2011 | Opsal et al. | |
| 9,915,522 B1 | 3/2018 | Jiang et al. | |
| 2015/0219529 A1 | 8/2015 | Akiyama et al. | |
| 2015/0277438 A1* | 10/2015 | Chen ...................... | G02B 5/281 700/97 |

FOREIGN PATENT DOCUMENTS

| | | |
|---|---|---|
| WO | 2014100037 A1 | 6/2014 |
| WO | 2014123907 A1 | 8/2014 |
| WO | 2016158785 A1 | 1/2018 |

OTHER PUBLICATIONS

International Search Report and Written Opinion dated Oct. 31, 2018 for PCT/US2018/043592.

Kidwai, Omar et al., "Effective-medium approach to planar multilayer hyperbolic meta materials: Strengths and limitations", Physical Review A. May 31, 2012, vol. 85, No. 5, pp. 053842(1)-053842(12).

* cited by examiner

MULTILAYER FILM METROLOGY USING AN EFFECTIVE MEDIA APPROXIMATION

CROSS-REFERENCE TO RELATED APPLICATION

The present application claims the benefit under 35 U.S.C. § 119(e) of U.S. Provisional Application Ser. No. 62/536,880, filed Jul. 25, 2017, entitled 3DFlash Film Measurement Employing an Effective Media Approximation, naming Mark Allen Neil, Mikhail Sushchik, and Natalia Malkova as inventors, which is incorporated herein by reference in the entirety.

TECHNICAL FIELD

The present disclosure relates generally to film metrology and, more particularly, to measurements of multilayer film stacks.

BACKGROUND

Production lines typically incorporate metrology measurements on representative samples and/or locations on samples to monitor process variations and ensure that fabrication remains within quality tolerances. Accordingly, metrology recipes defining the number, location, and frequency of metrology measurements are typically carefully designed to balance the accuracy of metrology measurements, the number of representative metrology measurements, and the measurement throughput to achieve a desired level of fabrication accuracy within a reasonable timeframe. Metrology throughput is therefore a critical consideration in semiconductor metrology systems and increases in metrology throughput may facilitate tighter process control and/or increased total production throughput of a semiconductor process.

Multilayer film stacks such as, but not limited to, three-dimensional (3D) flash memory devices present particular challenges that may limit metrology throughput since each layer is typically not directly characterized. For example, multilayer film metrology typically relies on modeling to extract parameters of interest (e.g., average film thickness, or the like) from a measurement. It may therefore be desirable to provide a system and method for efficient multilayer metrology.

SUMMARY

A metrology system is disclosed in accordance with one or more illustrative embodiments of the present disclosure. In one illustrative embodiment, the system includes a controller coupled to a detector to generate a detection signal based on reflection of an illumination beam from a multilayer film stack. In another illustrative embodiment, the multilayer film stack includes one or more zones with two or more material compositions disposed in a repeating pattern, where a number of layers of each material composition within the one or more zones is known. In another illustrative embodiment, the controller models reflection of the illumination beam by the multilayer film stack by modeling the one or more zones of repeating layers of the multilayer film stack as thick films having zone thicknesses and effective permittivity values using an effective medium model relating the effective permittivity values of the one or more zones to permittivity values of the two or more material compositions and volume fractions of the two or more material compositions within the one or more zones. In another illustrative embodiment, the controller determines values of the zone thicknesses and the volume fractions using a regression of the detection signal based on the effective medium model. In another illustrative embodiment, the controller determines average thickness values of the two or more material compositions within the one or more zones based on the number of films having each of the two or more material compositions, the zone thicknesses, the volume fractions, and the effective permittivity values.

A metrology system is disclosed in accordance with one or more illustrative embodiments of the present disclosure. In one illustrative embodiment, the system includes an illumination source to generate an illumination beam. In another illustrative embodiment, the system includes one or more illumination optical elements configured to direct the illumination beam to a multilayer film stack. In another illustrative embodiment, the multilayer film stack includes one or more zones with two or more material compositions disposed in a repeating pattern, where a number of layers of each material composition within the one or more zones is known. In another illustrative embodiment, the system includes one or more collection optical elements configured to capture reflected light from the multilayer film stack in response to the illumination beam. In another illustrative embodiment, the system includes a detector to generate a detection signal based on the light captured by the one or more collection optical elements. In another illustrative embodiment, the system includes a controller. In another illustrative embodiment, the controller models reflection of the illumination beam by the multilayer film stack by modeling the one or more zones of repeating layers of the multilayer film stack as thick films having zone thicknesses and effective permittivity values using an effective medium model relating the effective permittivity values of the one or more zones to permittivity values of the two or more material compositions and volume fractions of the two or more material compositions within the one or more zones. In another illustrative embodiment, the controller determines values of the zone thicknesses and the volume fractions using a regression of the detection signal based on the effective medium model. In another illustrative embodiment, the controller determines average thickness values of the two or more material compositions within the one or more zones based on the number of films having each of the two or more material compositions, the zone thicknesses, the volume fractions, and the effective permittivity values.

A method for determining layer thicknesses of a multilayer film is disclosed in accordance with one or more illustrative embodiments of the present disclosure. In one illustrative embodiment, the method includes measuring light reflected from a multilayer film stack to generate a detection signal. In another illustrative embodiment, the multilayer film stack includes one or more zones with two or more material compositions disposed in a repeating pattern, where a number of layers of each material composition within the one or more zones is known. In another illustrative embodiment, the method includes modeling reflection of the light by the multilayer film stack by modeling the one or more zones of repeating layers of the multilayer film stack as thick films having zone thicknesses and effective permittivity values using an effective medium model relating the effective permittivity values of the one or more zones to permittivity values of the two or more material compositions and volume fractions of the two or more material compositions within the one or more zones. In another illustrative embodiment, the method includes determining values of the zone thicknesses and the volume fractions using a regression of the detection signal based on the effective medium model. In another illustrative embodiment, the method includes determining average thickness values of the two or more material compositions within the one or more zones based on the number of films having each of the two or more material compositions, the zone thicknesses, the volume fractions, and the effective permittivity values.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which.

DETAILED DESCRIPTION

Figure 1A:
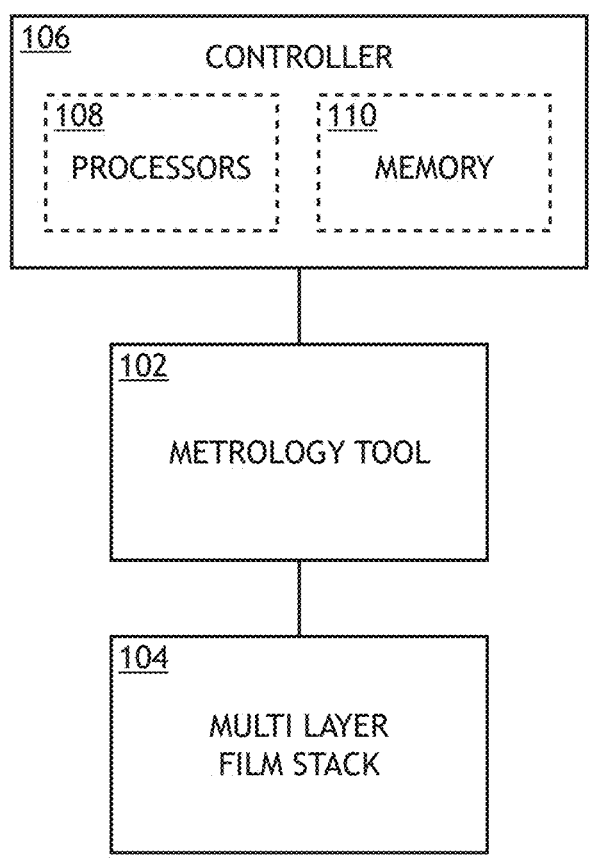
FIG. 1A is a conceptual view illustrating a semiconductor device fabrication system, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Embodiments of the present disclosure are directed to metrology of a multilayer film stack having alternating layers of different film compositions based on modeling the multilayer film stack with an effective medium approximation (EMA) model.

Multilayer film stacks in semiconductor devices typically include a known number of repeating layers of defined compositions. For example, a 3D flash memory device may include, but is not required to include, approximately 100 alternating layers of an oxide material and a nitride material with known target thicknesses. However, process variations during fabrication may lead to corresponding variations of fabricated characteristics of the films such as, but not limited to, the average film thickness or the permittivity values of the layers. It is recognized herein that direct measurements of the characteristics of each constituent film of a film stack may not be desirable or practical. Additional embodiments of the present disclosure are directed to modeling a multilayer film stack as a single film with an effective permittivity using an effective medium model, measuring global characteristics of the multilayer film stack, and extracting the properties of the constituent layers based on the model and the measured global characteristics.

Additional embodiments of the present disclosure are directed to modeling repeating layers of a multilayer film stack using an EMA model as a single film with an effective permittivity value based on permittivity values of the constituent materials (e.g., the oxide layers and the nitride layers) and fraction factors describing the volume fractions of the constituent materials within the film stack (e.g., within a sequence of repeating layers). The EMA model may define relationships between the permittivity values of the constituent layers and the volume fractions based on any number of factors such as, but not limited to, a physical distribution of the constituent materials, local electrostatic effects, or material anisotropy. Additionally, the EMA model may include any type of EMA model known in the art such as, but not limited to, a Maxwell-Garnett model or a Bruggeman model. Further, the EMA model may incorporate modified versions of EMA models known in the art.

Multilayer film stacks may further include components in addition to a sequence of repeating layers. For example, a multilayer stack may include one or more non-repeating layers (e.g., a top layer, a bottom layer, or the like). By way of another example, a multilayer stack may include multiple instances, or zones, of repeating layers. For instance, a multilayer stack may include a first zone including repeating oxide and nitride layers, a thick intermediate layer, a second zone including repeating oxide and nitride layers, and so on. Further, the multiple zones of repeating layers need not be the same. In this regard, the number of layers and/or the compositions of the layers in each zone may vary.

Additional embodiments of the present disclosure are directed to modeling the reflectance of light by a multilayer film stack based on the EMA model. For example, reflectance of light by a multilayer film stack may be modeled based on considering the zones of repeating film layers as thick films with an effective index based on the EMA model, as well as any non-repeating layers.

Additional embodiments of the present disclosure are directed to measuring global characteristics of the multilayer film stack. For example, the effective permittivity of the multilayer film stack may be determined based on the properties of light reflected from the multilayer film stack using optical techniques such as, but not limited to, reflectometry or ellipsometry. In some embodiments, characteristics of the multilayer film stack are determined based on narrow-band measurements such as, but not limited to, single-wavelength reflectometry, single-wavelength ellipsometry, angle-resolved reflectometry, or angle-resolved ellipsometry. In some embodiments, characteristics of the multilayer film stack are determined based on broadband (e.g., multi-wavelength) measurements such as, but not limited to, spectroscopic reflectometry or spectroscopic ellipsometry.

Additional embodiments of the present disclosure are directed to applying a regression analysis to determine values of unknown parameters of the EMA-based reflectance model of the multilayer film stack based on the measured global characteristics of the multilayer film stack. Depending on the application, any combination of parameters associated with the EMA model may be fit based on the measured data such as, but not limited to, the total thickness of the multilayer film stack, the thicknesses of any zones of repeating layers, the volume fractions of compositions in any zones of repeating layers, or the permittivity values of any of the constituent layers.

For example, it may be the case that the permittivity values of the constituent film layers are known or may be approximated within an acceptable accuracy requirement, but the exact thicknesses of the fabricated film layers may be unknown. In this regard, process variations during film deposition may lead to variations in the exact thicknesses of the deposited films. Accordingly, a regression analysis of a single zone of repeating layers may incorporate permittivity values of the constituent films as independent variables and may determine values of the total thickness of the zone and the fraction factors based on a fit to measured reflectivity values of the multilayer film stack. The average thicknesses of the constituent layers may then be determined based on the total thickness and the fraction factors provided by the regression analysis as well as known information regarding the stack such as the number of layers of each type of material. For instance, the average thicknesses, $T_i$, of layers of a given composition in a zone may be characterized as:

$$T_i = \frac{f_{v,i} T_{tot}}{N_i}, \text{ for } i = 1 \dots n, \text{ and } \sum_i f_{v,i} = 1. \tag{1}$$

where $T_{tot}$ is the total thickness of the zone, n is the number of types of layers (e.g., layers of different composition), $N_i$ is the number of layers of each composition, and $f_{v,i}$ is the volume fraction associated with each composition within the zone. Further, the constraint of $\Sigma_i f_{v,i}=1$ provides that the zone is divided into the layers of interest.

Additionally, in the case that a multilayer film stack includes multiple zones of repeating layers and/or non-repeating film layers (e.g., top layers, intermediate layers, bottom layers, or the like), a regression analysis may separately fit values associated with each zone and/or each non-repeating film layer.

It is recognized herein that extracting average values of the layer thicknesses based on the modeling a multilayer film stack as an effective medium may provide high-throughput metrology. For example, modeling a multilayer film stack as an effective medium may substantially reduce computation time relative to a direct modeling approach including an estimation phase involving a gridded search over expected process windows of the layers being measured to estimate the average thicknesses of the constituent layers followed by a solution phase to solve for the individual layer thicknesses. In a non-limiting example, an effective medium modeling approach reduced the computation time for multilayer stacks having approximately 100 alternating oxide and nitride layers by approximately 50% relative to a two-phase direct modeling approach without reducing accuracy.

FIG. 1A is a conceptual view illustrating a semiconductor device fabrication system 100, in accordance with one or more embodiments of the present disclosure. In one embodiment, the system 100 includes a metrology tool 102 configured to characterize one or more properties of a multilayer film stack 104. In another embodiment, the system 100 includes a controller 106 communicatively coupled to the metrology tool 102. In another embodiment, the controller 106 includes one or more processors 108 configured to execute program instructions maintained on a memory medium 110, or memory. The one or more processors 108 of a controller 106 may include any processing element known in the art. In this sense, the one or more processors 108 may include any microprocessor-type device configured to execute algorithms and/or instructions. Further, the memory medium 110 may include any storage medium known in the art suitable for storing program instructions executable by the associated one or more processors 108. For example, the memory medium 110 may include a non-transitory memory medium. As an additional example, the memory medium 110 may include, but is not limited to, a read-only memory (ROM), a random-access memory (RAM), a magnetic or optical memory device (e.g., disk), a magnetic tape, a solid-state drive and the like. It is further noted that memory medium 110 may be housed in a common controller housing with the one or more processors 108.

In this regard, the one or more processors 108 of the controller 106 may execute any of the various process steps described throughout the present disclosure. For example, the one or more processors 108 of controller 106 may receive, generate and/or implement an EMA model of multilayer film stacks 104, perform regression analyses to determine values of dependent variables based on the EMA model and measured data from the metrology tool 102 associated with multilayer film stacks 104.

Figure 1B:
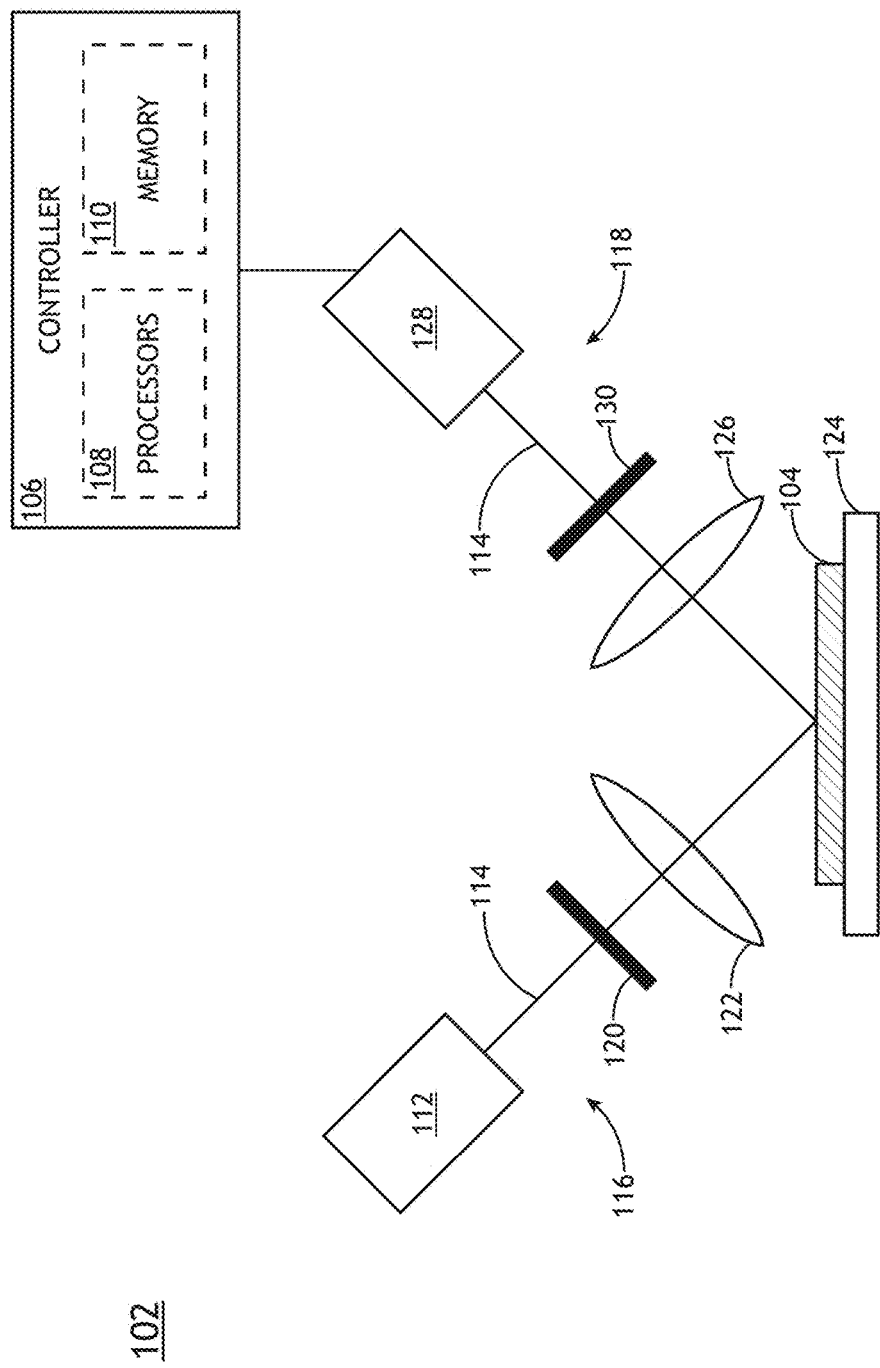
FIG. 1B is a conceptual view illustrating a metrology tool, in accordance with one or more embodiments of the present disclosure.

FIG. 1B is a conceptual view illustrating a metrology tool 102, in accordance with one or more embodiments of the present disclosure.

The metrology tool 102 may include any type of metrology system known in the art suitable for providing metrology signals associated with metrology targets on a multilayer film stack 104. In one embodiment, the metrology tool 102 is configured to provide signals indicative of one or more optical properties of a metrology target (e.g., one or more dispersion parameters, and the like) at one or more wavelengths. For example, the metrology tool 102 may include, but is not limited to, a spectrometer, a spectroscopic ellipsometer with one or more angles of illumination, a spectroscopic ellipsometer for measuring Mueller matrix elements (e.g., using rotating compensators), a single-wavelength ellipsometer, an angle-resolved ellipsometer (e.g., a beam-profile ellipsometer), a spectroscopic reflectometer, a single-wavelength reflectometer, an angle-resolved reflectometer (e.g., a beam-profile reflectometer), an imaging system, a pupil imaging system, a spectral imaging system, or a scatterometer. In one embodiment, the metrology tool 102 includes an image-based metrology tool to measure metrology data based on the generation of one or more images of a sample.

In one embodiment, the metrology tool 102 includes an illumination source 112 to generate an illumination beam 114. The illumination beam 114 may include one or more selected wavelengths of light including, but not limited to, ultraviolet (UV) radiation, visible radiation, or infrared (IR) radiation. For example, the illumination source 112 may provide, but is not required to provide, an illumination beam 114 having wavelengths in the range of approximately 600 nm to approximately 800 nm.

The illumination source 112 may include, but is not limited to, one or more narrowband laser sources, one or more broadband laser sources, one or more supercontinuum laser sources, one or more white light laser sources, and the like. In another embodiment, the illumination source 112 includes a laser-driven light source (LDLS) such as, but not limited to, a laser-sustained plasma (LSP) source. For example, the illumination source 112 may include, but is not limited to, an LSP lamp, an LSP bulb, or an LSP chamber suitable for containing one or more elements that, when excited by a laser source into a plasma state, may emit broadband illumination. In this regard, the illumination source 112 may provide an illumination beam 114 having high coherence (e.g., high spatial coherence and/or temporal coherence). In another embodiment, the illumination source 112 includes a lamp source. By way of another example, the illumination source 112 may include, but is not limited to, an arc lamp, a discharge lamp, an electrode-less lamp, and the like. In this regard, the illumination source 112 may provide an illumination beam 114 having low coherence (e.g., low spatial coherence and/or temporal coherence).

In another embodiment, the illumination source 112 provides a tunable illumination beam 114. For example, the illumination source 112 may include a tunable source of illumination (e.g., one or more tunable lasers, and the like). By way of another example, the illumination source 112 may include a broadband illumination source coupled to a tunable filter.

The illumination source 112 may further provide an illumination beam 114 having any temporal profile. For example, the illumination beam 114 may have a continuous temporal profile, a modulated temporal profile, a pulsed temporal profile, and the like.

In another embodiment, the illumination source 112 directs the illumination beam 114 to the multilayer film stack 104 via an illumination pathway 116 and collects radiation emanating from the sample via a collection pathway 118. The illumination pathway 116 may include one or more beam conditioning components 120 suitable for modifying and/or conditioning the illumination beam 114. For example, the one or more beam conditioning components 120 may include, but are not limited to, one or more polarizers, one or more filters, one or more beam splitters, one or more diffusers, one or more homogenizers, one or more apodizers, one or more beam shapers, or one or more lenses.

In another embodiment, the illumination pathway 116 may utilize a first focusing element 122 to focus the illumination beam 114 onto the multilayer film stack 104 disposed on a sample stage 124. In another embodiment, the collection pathway 118 may include a second focusing element 126 to collect radiation from the multilayer film stack 104.

In another embodiment, the metrology tool 102 includes a detector 128 configured to capture radiation emanating from the multilayer film stack 104 through the collection pathway 118. For example, a detector 128 may receive radiation reflected or scattered (e.g., via specular reflection, diffuse reflection, and the like) from the multilayer film stack 104. By way of another example, a detector 128 may receive radiation generated by the multilayer film stack 104 (e.g., luminescence associated with absorption of the illumination beam 114, and the like).

The detector 128 may include any type of optical detector known in the art suitable for measuring illumination received from the multilayer film stack 104. For example, a detector 128 may include, but is not limited to, a charge-coupled device (CCD) detector, a complementary metal-oxide semiconductor (CMOS) detector, a time-delay integration (TDI) detector, a photomultiplier tube (PMT), an avalanche photodiode (APD), and the like. In another embodiment, a detector 128 may include a spectroscopic detector suitable for identifying wavelengths of radiation emanating from the multilayer film stack 104.

The collection pathway 118 may further include any number of collection beam conditioning elements 130 to direct and/or modify illumination collected by the second focusing element 126 including, but not limited to one or more lenses, one or more filters, one or more polarizers, or one or more phase plates. In this regard, the metrology tool 102 may be configured as any type of metrology tool such as, but not limited to, a spectroscopic ellipsometer with one or more angles of illumination, a spectroscopic ellipsometer for measuring Mueller matrix elements (e.g., using rotating compensators), a single-wavelength ellipsometer, an angle-resolved ellipsometer (e.g., a beam-profile ellipsometer), a spectroscopic reflectometer, a single-wavelength reflectometer, an angle-resolved reflectometer (e.g., a beam-profile reflectometer), an imaging system, a pupil imaging system, a spectral imaging system, or a scatterometer.

Further, it is noted herein that the metrology tool 102 depicted in FIG. 1B may facilitate multi-angle illumination of the multilayer film stack 104, and/or more than one illumination source 112 (e.g., coupled to one or more additional detectors 128). In this regard, the metrology tool 102 depicted in FIG. 1D may perform multiple metrology measurements. In another embodiment, one or more optical components may be mounted to a rotatable arm (not shown) pivoting around the multilayer film stack 104 such that the angle of incidence of the illumination beam 114 on the multilayer film stack 104 may be controlled by the position of the rotatable arm. In another embodiment, the metrology tool 102 may include multiple detectors 128 (e.g., associated with multiple beam paths generated by one or more beam-splitters) to facilitate multiple metrology measurements (e.g., multiple metrology tools) by the metrology tool 102.

In another embodiment, though not shown, the metrology tool 102 includes a chamber suitable for regulating the composition and/or the pressure of the atmosphere surrounding the multilayer film stack 104. For example, the metrology tool 102 may include one or more gas tanks, one or more valves, one or more hoses, one or more pumps, one or more pressure regulators, and the like to control the composition and/or pressure of the atmosphere surrounding the multilayer film stack 104. In another embodiment, the metrology tool 102 is configured to provide an inert gas or a gas substantially transparent to wavelengths provided by the illumination source 112 as an atmosphere surrounding the multilayer film stack 104.

Figure 1C:
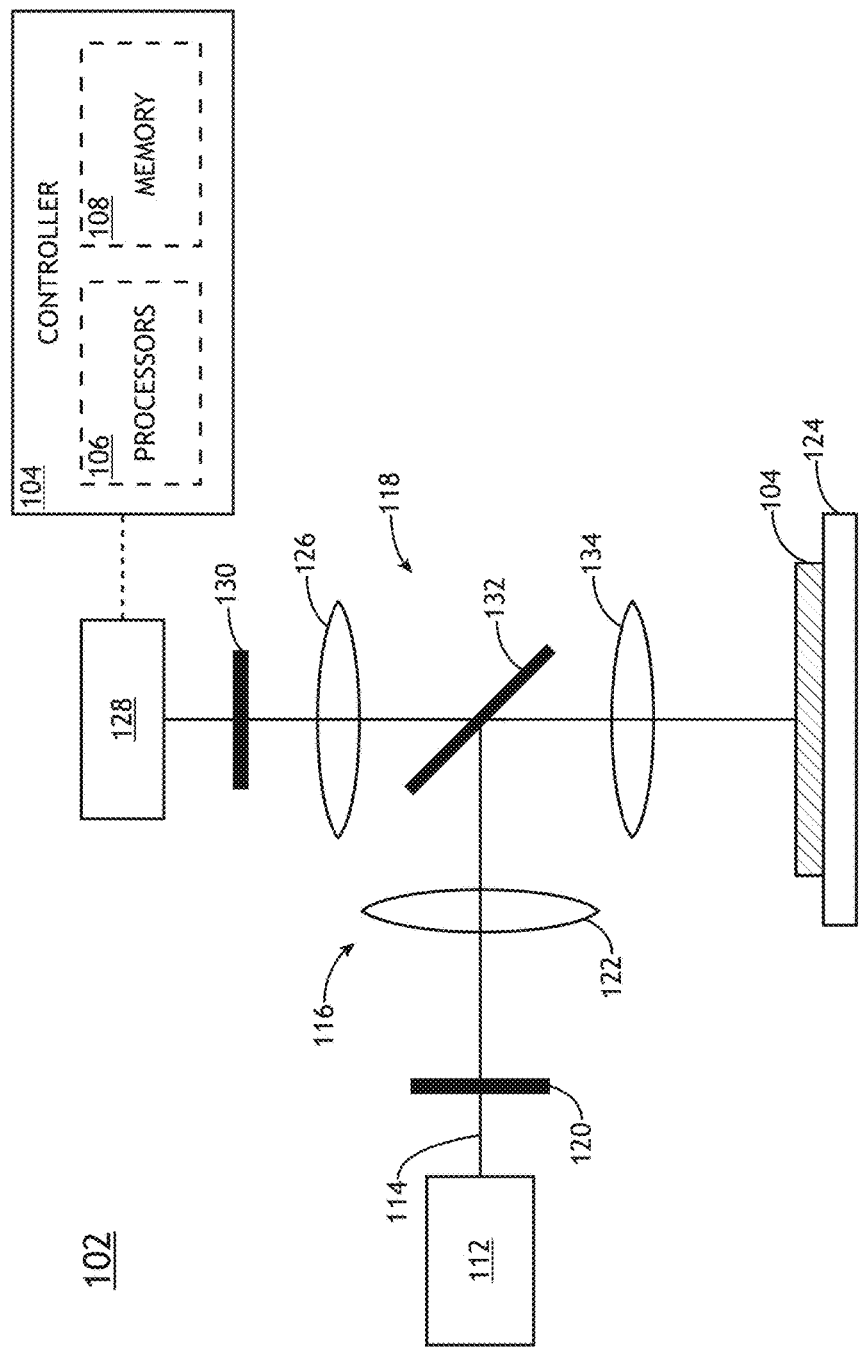
FIG. 1C is a conceptual view illustrating a metrology tool configured with a single illumination and collection optical element, in accordance with one or more embodiments of the present disclosure.

FIG. 1C is a conceptual view illustrating a metrology tool 102 configured with a single illumination and collection optical element, in accordance with one or more embodiments of the present disclosure. In one embodiment, the metrology tool 102 includes a beamsplitter 132 oriented such that an objective lens 134 may simultaneously direct the illumination beam 114 to the multilayer film stack 104 and collect radiation emanating from the multilayer film stack 104.

Further, the metrology system may include a single metrology tool or multiple metrology tools. A metrology system incorporating multiple metrology tools is generally described in U.S. Pat. No. 7,933,026 titled "High resolution monitoring of CD variations" issued on Apr. 26, 2011, and U.S. Pat. No. 7,478,019 titled "Multiple tool and structure analysis" issued on Jan. 13, 2009, both of which are incorporated herein by reference in their entirety. Focused beam ellipsometry based on primarily reflective optics is generally described in U.S. Pat. No. 5,608,526 titled "Focused beam spectroscopic ellipsometry method and system" issued on Mar. 4, 1997, which is incorporated herein by reference in its entirety. The use of apodizers to mitigate the effects of optical diffraction causing the spread of the illumination spot beyond the size defined by geometric optics is generally described in U.S. Pat. No. 5,859,424 titled "Apodizing filter system useful for reducing spot size in optical measurements and other applications" issued on Jan. 12, 1999, which is incorporated herein by reference in its entirety. The use of high-numerical-aperture tools with simultaneous multiple angle-of-incidence illumination is generally described by U.S. Pat. No. 6,429,943 titled "Critical dimension analysis with simultaneous multiple angle of incidence measurements" issued on Aug. 6, 2002, which is incorporated herein by reference in its entirety.

Figure 2:
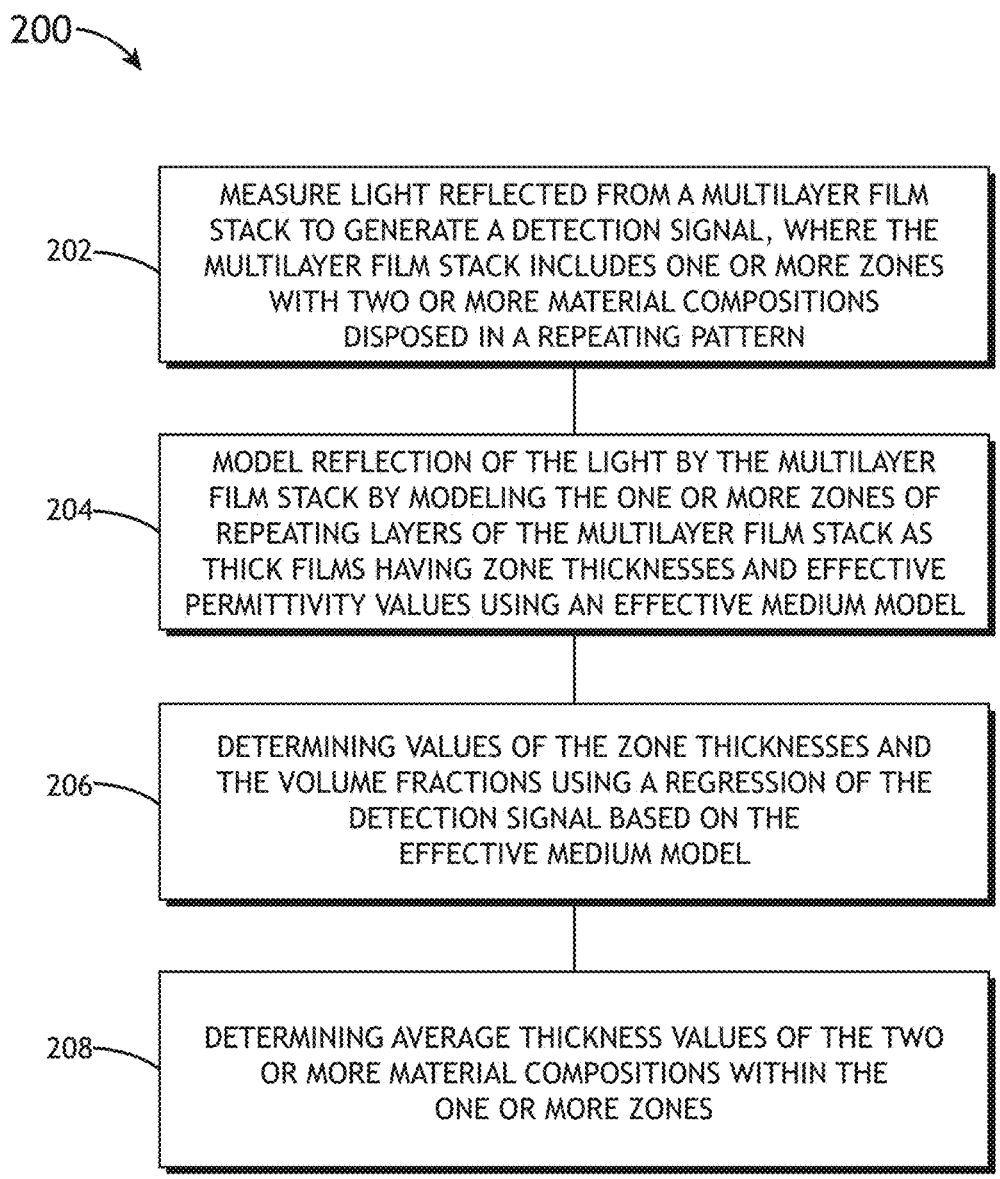
FIG. 2 is a flow diagram illustrating steps performed in a method for determining layer thicknesses of a multilayer film, in accordance with one or more embodiments of the present disclosure.

FIG. 2 is a flow diagram illustrating steps performed in a method 200 for determining layer thicknesses of a multilayer film, in accordance with one or more embodiments of the present disclosure. Applicant notes that the embodiments and enabling technologies described previously herein in the context of the system 100 should be interpreted to extend to method 200. It is further noted, however, that the method 200 is not limited to the architecture of the system 100.

In one embodiment, the method 200 includes a step 202 of measuring light reflected from a multilayer film stack including one or more zones with two or more material compositions disposed in a repeating pattern to generate a detection signal. The step 202 may be performed, but is not required to be performed, using the system 100 illustrated in FIGS. 1A through 1C.

Figure 3A:
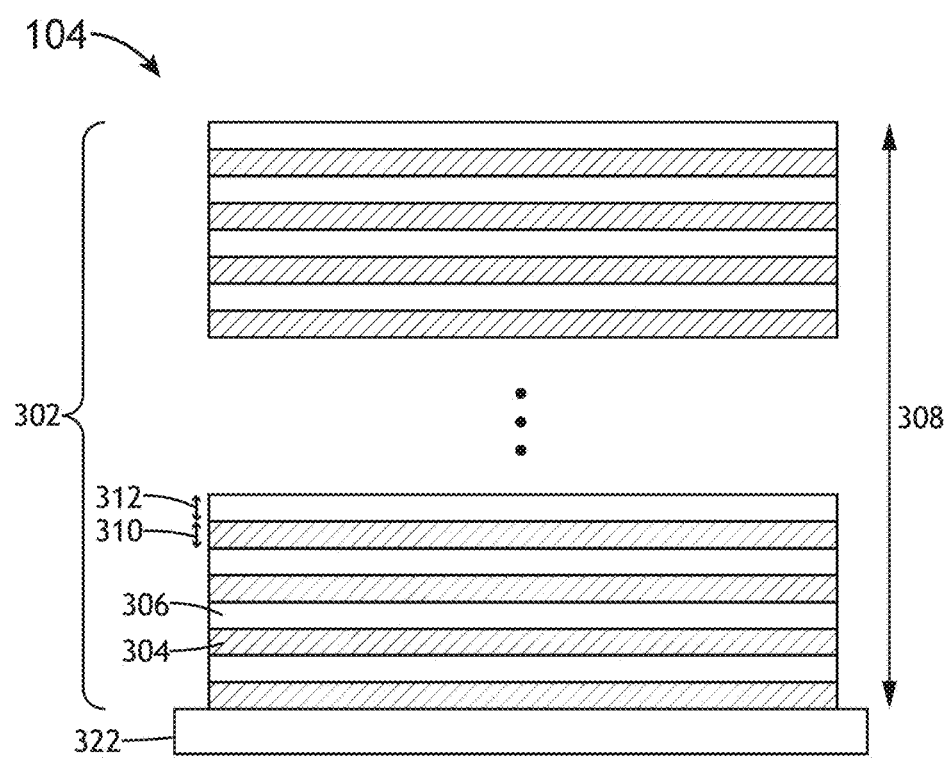
FIG. 3A is a side view of a multilayer film stack including repeating film layers, in accordance with one or more embodiments of the present disclosure.

FIG. 3A is a side view of a multilayer film stack 104 including repeating film layers 302 (e.g., a single zone of repeating layers), in accordance with one or more embodiments of the present disclosure. The multilayer film stack 104 may include any number of films having various compositions such as, but not limited to, dielectric materials (e.g., oxide materials, nitride materials, fluoride materials, or the like), metals, ceramics, or polymers. In one embodiment, the repeating film layers 302 are formed from a first composition 304 and a second composition 306 deposited in an alternating pattern.

In another embodiment, film layers of each composition have a target thickness, though it may be the case that the thicknesses of fabricated layers may deviate from the target thicknesses due to variations in process conditions. Accordingly, a total zone thickness 308 of a sequence of repeating layers 302 may vary based on the process variations. For example, film layers having the first composition 304 may have a first target thickness 310 and film layers having the second composition 306 may have a second target thickness 312. Further, film layers having different compositions may have the same target thicknesses or different target thicknesses.

By way of a non-limiting example, a multilayer film stack 104 associated with a 3D flash memory device may include 96 layer pairs of an oxide material with a target thickness of 400 Angstroms and a nitride material with a target thickness of 200 Angstroms. In this regard, the first composition 304 may correspond to the oxide material, the first target thickness 310 may correspond to 400 Angstroms, the second composition 306 may correspond to the nitride material, and the second target thickness 312 may correspond to 200 Angstroms.

Figure 3B:
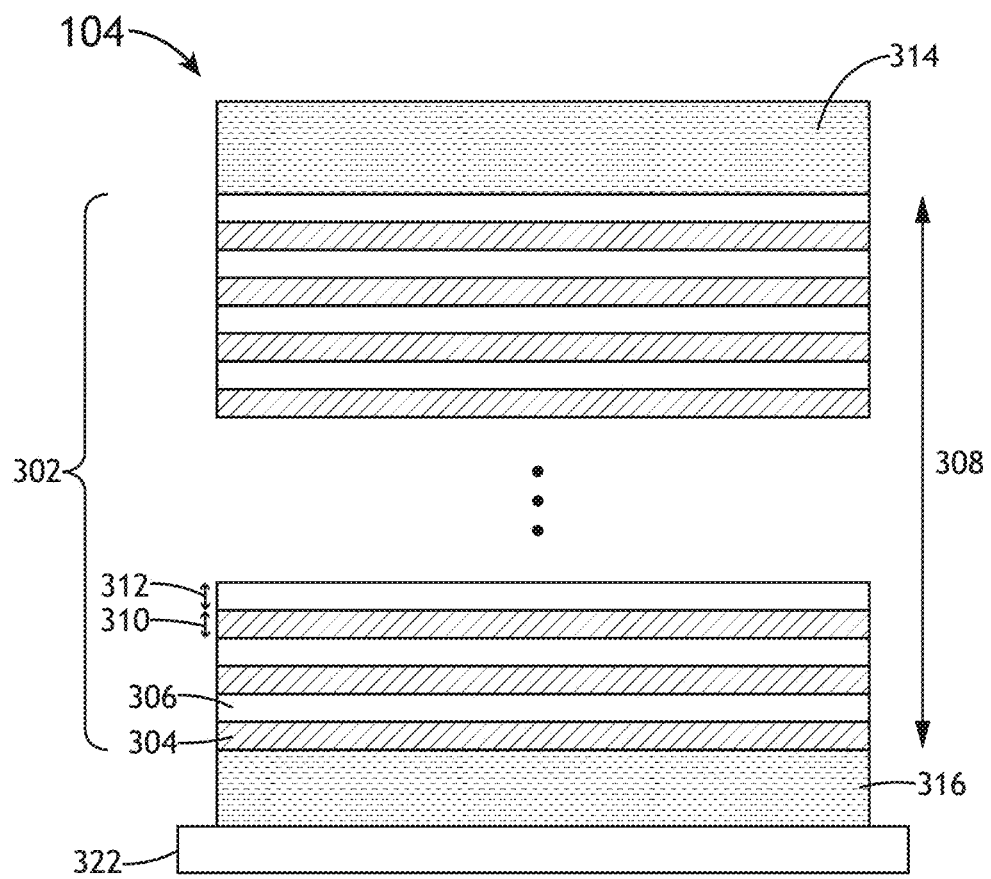
FIG. 3B is a side view of a multilayer film stack including repeating film layers, a top layer, and a bottom layer, in accordance with one or more embodiments of the present disclosure.

In another embodiment, a multilayer film stack 104 may include additional layers (e.g., non-repeating layers) such as, but not limited to, a top layer (e.g., a cap layer, or the like) or a bottom layer. The additional layers may be formed from any of the material compositions of the repeating film layers 302 or may be formed from additional material compositions. Further, the additional layers may have the same or different target thicknesses (e.g., the first target thickness 310 or the second target thickness 312) as the repeating film layers 302. FIG. 3B is a side view of a multilayer film stack 104 including repeating film layers 302, a top layer 314, and a bottom layer 316, in accordance with one or more embodiments of the present disclosure. For example, as illustrated in FIG. 3B, the top layer 314 and/or the bottom layer 316 may be formed from the same compositions as the repeating film layers 302 and may further continue the repeating pattern of the repeating film layers 302. However, as further illustrated in FIG. 3B, the top layer 314 and/or the bottom layer 316 may have different thicknesses as the repeating film layers 302.

Figure 3C:
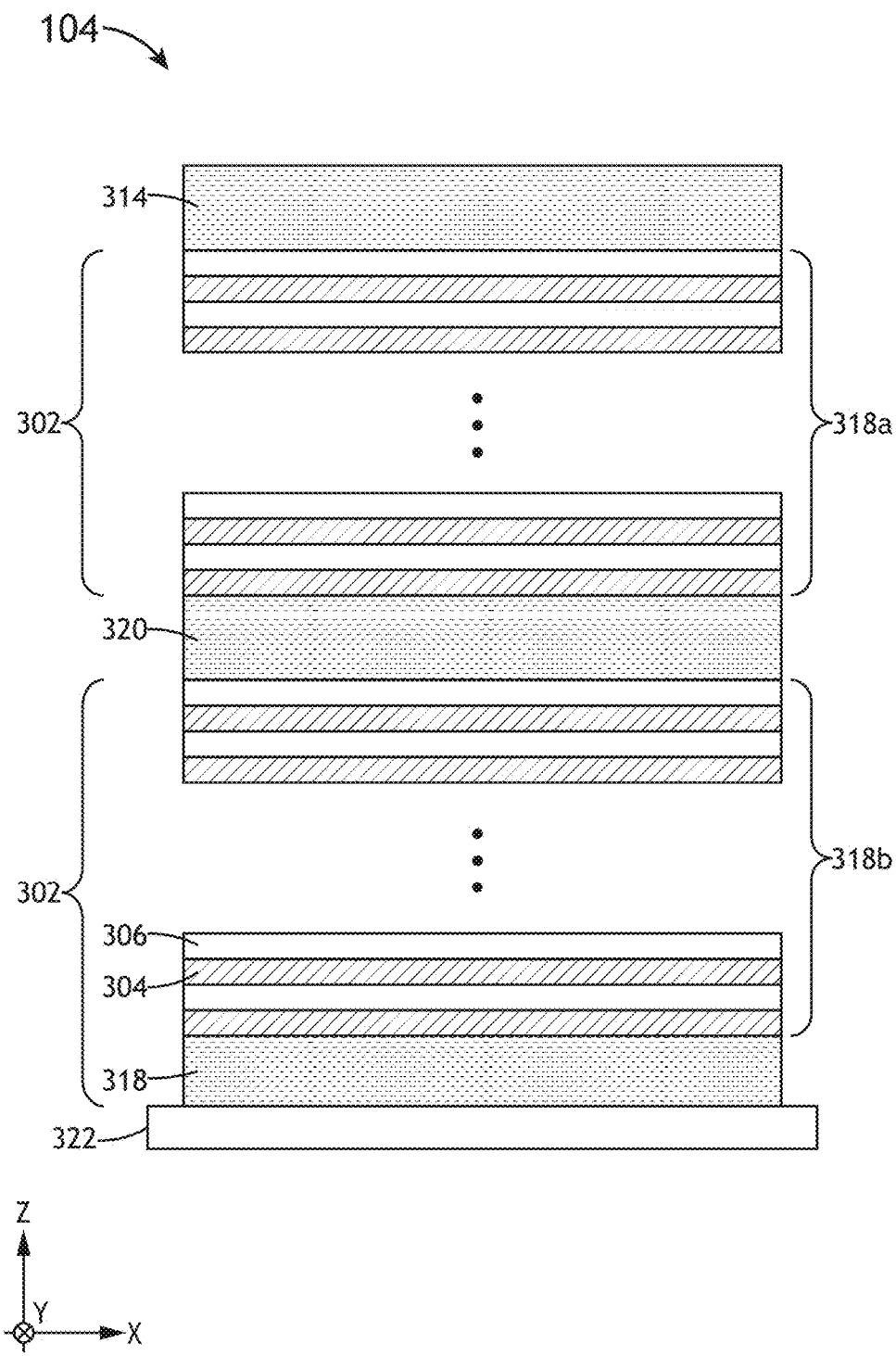
FIG. 3C is a side view of a multilayer film stack including two zones of repeating film layers separated by non-repeating layers, in accordance with one or more embodiments of the present disclosure.

A multilayer film stack 104 may include multiple instances, or zones, of repeating film layers 302 and/or non-repeating layers. FIG. 3C is a side view of a multilayer film stack 104 including two zones of repeating film layers separated by non-repeating layers, in accordance with one or more embodiments of the present disclosure. In one embodiment, a multilayer film stack 104 includes a first zone 318a of repeating layers 302 and a second zone 318b of repeating layers 302. For example, as illustrated in FIG. 3C, the first zone 318a and the second zone 318b include alternating layers of the first composition 304 and the second composition 306.

However, it is to be understood that the illustration of the zones of repeating layers 302 in FIG. 3C is provided solely for illustrative purposes and should not be interpreted as limiting. The characteristics of different zones of repeating layers 302 (e.g., zones 318a and 318b) such as, but not limited to, the number of films, the order of films, the composition of films, or the thicknesses of films may be the same or may vary.

In another embodiment, also illustrated in FIG. 3C, the multilayer film stack 104 includes an intermediate layer 320 between the first zone 318a and the second zone 318b. The multilayer film stack 104 may additionally include one or more additional non-repeating layers such as, but not limited to, a top layer 314 and/or a bottom layer 316. The non-repeating layers (e.g., the intermediate layer 320, the top layer 314, the bottom layer 316, or the like) may have any thickness and may further have any composition. For example, the non-repeating layers may have a different composition than any of the repeating layers 302 or may have a composition corresponding to any of the repeating layers.

It is to be understood that the illustration of a multilayer film stack 104 including two film compositions in an alternating pattern illustrated in FIGS. 3A through 3C are provided solely for illustrative purposes and should not be interpreted as limiting. As described previously herein, a multilayer film stack 104 may include any number of layers in a repeating pattern. For example, repeating film layers 302 may include three or more compositions in a repeating pattern.

In another embodiment, the repeating film layers 302 may be deposited on a substrate 322. For example, the substrate 322 may provide, but is not required to provide, mechanical support for the repeating film layers 302. The substrate 322 may be any type of material such as, but not limited to, a semiconductor material (e.g., a semiconductor wafer, or the like), a dielectric material, a metal, or an organic material, a ceramic, or a polymer.

In one embodiment, the step 202 includes measuring light reflected from a multilayer film stack 104 (e.g., as illustrated in FIGS. 3A through 3C, or the like) using any combination of reflectometry or ellipsometry. For example, the step 202 may include measuring a difference between the intensity of incident and reflected light for one or more wavelengths and/or at one or more angles of illumination. Further, polarization-sensitive measurements may be performed by controlling the polarization of incident illumination (e.g., via the beam conditioning components 120, or the like) and/or by monitoring the polarization of reflected light (e.g., via the collection beam conditioning elements 130).

It is recognized herein that effective medium index models typically require that the measurement wavelength is substantially greater than the thicknesses of the sizes of the constituent materials within the repeating layers 302. Accordingly, the wavelength or wavelengths of illumination associated with the measurement in step 202 may be selected based on the target thicknesses of the constituent layers (e.g., the first target thickness 310, the second target thickness 312, or the like). For example, a multilayer film stack 104 associated with 3D flash memory may include, but is not required to include, repeating film layers 302 having target thicknesses between approximately 200 Angstroms to approximately 400 Angstroms. Accordingly, wavelengths of illumination suitable for characterizing the multilayer film stack 104 may be, but are not required to be, larger than approximately 600 nm. In this regard, the wavelengths of illumination may be at least an order of magnitude larger than sum of the target thicknesses of the constituent layers.

In another embodiment, the method 200 includes a step 204 of modeling reflection of the broadband light by the multilayer film stack 104 by modeling the one or more zones of repeating layers of the multilayer film stack as thick films having zone thicknesses (e.g., zone thicknesses 308) and effective permittivity values using an effective medium model. For example, the effective medium model relates the permittivity values of constituent material layers (e.g., the repeating film layers 302, or the like) to an effective permittivity of a zone of repeating layers 302 based on the volume fractions of the constituent material layers.

The effective medium model may relate an effective permittivity of a zone of repeating layers 302 to the permittivity values of the known constituent material compositions (e.g., the first composition 304, the second composition 306, or the like) based on any combination of factors including, but not limited to, the physical layout of the constituent materials, local electrostatic effects, polarizability, or material anisotropy. Further, the effective medium model may incorporate in full or in part aspects of any effective medium model known in the art such as, but not limited to, a Maxwell Garnett model or a Bruggeman model.

In one embodiment, the effective medium model of step 204 may approximate a zone of repeating layers 302 as spatially uniform and isotropic on average. In this regard, the zone of repeating layers 302 may be considered to have uniformly-distributed inclusions on length scales smaller than the wavelength of measurement light used in step 202. For example, a Maxwell Garnett effective medium model considering a host material with spatially-uniform spherical inclusions may be modeled as an isotropic material.

In another embodiment, the effective medium model of step 204 may approximate a zone of repeating layers 302 as a uniaxial material. For example, referring again to FIGS. 3A and 3B, the direction perpendicular to the substrate 322 (e.g., the Z direction) may be considered as the optic axis. In this regard, the zone of repeating layers 302 may be modeled as having an extraordinary refractive index along the Z direction and an ordinary refractive index for directions along the X-Y plane. For example, the effective permittivity of a two-composition zone (e.g., as illustrated in FIGS. 3A through 3C, or the like) may be, but is not required to be, characterized as an effective permittivity tensor:

$$\hat{\epsilon} = \mathrm{diag}(\epsilon_t, \epsilon_t, \epsilon_z), \quad (2)$$

where $\epsilon_t$ is a transverse permittivity along directions in the X-Y plane and $\epsilon_z$ is a permittivity along the Z direction based on the axes illustrated in FIGS. 3A through 3C. Further, the values of $\epsilon_t$ and $\epsilon_z$ may be functions of the permittivity values and the volume fractions of the constituent materials and may be, but are not required to be, characterized by the following expressions:

$$\epsilon_t = f_t(\epsilon_1, \epsilon_2, \ldots, \epsilon_m, f_{v,t,1}, f_{v,t,2}, \ldots, f_{v,t,n}), \epsilon_z = f_z(\epsilon_1, \epsilon_2, \ldots, \epsilon_m, f_{v,z,1}, f_{v,z,2}, \ldots, f_{v,z,n}) \quad (3)$$

where $f_t$ and $f_z$ are known functions, $\epsilon_1 \ldots \epsilon_n$ are the permittivity values of constituent compositions (e.g., the first composition 304, the second composition 306, or the like), and $f_{v,t,1} \ldots f_{v,t,n}$ are the volume fractions of the constituent compositions along the transverse direction within a zone, and $f_{v,z,1} \ldots f_{v,z,n}$ are the volume fractions of the constituent compositions along the Z direction within a zone. Further, the volume fractions may be separately constrained along different directions (e.g., $\Sigma_i f_{v,t,i} = 1$ and $\Sigma_i f_{v,z,i} = 1$) or may be constrained to be the same along all directions (e.g., $f_{v,t,i} = f_{v,z,i}$). In a general sense, any effective medium approximation may be implemented in step 204 based on the particular geometric and electrostatic considerations of a given zone of repeating layers. Additionally, different zones may be, but are not required to be, modeled using different effective medium approximation techniques.

In another embodiment, the step 204 includes modeling the reflection of light by the multilayer film stack 104 to provide a relationship between the measured detection signal of step 202, the one or more zones of repeating layers modeled as thick films based on the effective medium model, and any non-repeating layers (e.g., top layer 314, bottom layer 316, intermediate layers 320, or the like). For example, the model of the reflection of light by the multilayer film stack 104 may be based on any reflectometry or ellipsometry model known in the art relating the reflection of light from a multilayer film stack 104 to optical properties of the multilayer film stack 104.

Further, the permittivity values (and the corresponding refractive index values) of the constituent materials of the multilayer film stack 104 may be modeled using any dispersion model known in the art. In one embodiment, the permittivity values may be modeled as wavelength-independent values. In another embodiment, the permittivity values may vary as a function of wavelength. For example, the permittivity values for wavelengths of interest (e.g., wavelengths associated with the illumination source 112 used to generate the detection signal of step 202, or the like) may be based on experimental data. By way of another example, the permittivity values for wavelengths of interest may be expressed based on empirical relationships between wavelength and refractive index (directly related to the permittivity) such as, but not limited to, the Cauchy equation or the Sellmeier equations. By way of another example, the permittivity values for wavelengths of interest may be expressed using analytical dispersion models such as, but not limited to, Lorentz models, Tauc-Lorentz models, or the like. Further, the dispersion may be expressed, but is not required to be expressed, using any composite model.

In another embodiment, the method 200 includes a step 206 of determining values of the zone thicknesses and the volume fractions using a regression of the detection signal based on the effective medium model. For example, a regression analysis may be applied to determine values of the zone thicknesses (e.g., zone thickness 308 of FIGS. 3A through 3B, or the like) and the volume fractions, $f_i$, that provide a best "fit" to a model of the reflection of light by each zone of repeating layers 302 based on the effective medium approximation of step 204. In this regard, the zone thickness and the volume fractions, $f_{v,i}$, may be provided as unknown variables in a regression analysis and the permittivity values of the constituent materials may be provided as independent variables. Further, the regression of step 206 may be used to provide a best "fit" of unknown values (e.g., thicknesses or the like) of any non-repeating layers (e.g., the top layer 314, the bottom layer 316, the intermediate layers 320, or the like).

In another embodiment, the method 200 includes a step 208 of determining average thickness values of the constituent material compositions within the zones of repeating layers 302 based on the known number of films of each of the constituent material compositions, the zone thickness, the volume fractions, and the effective permittivity values for each zone. For example, the average thickness values of the constituent material compositions may be determined using Eq. (1) based on the zone thickness 308 and the volume fractions determined by regression in step 206.

Figure 4:
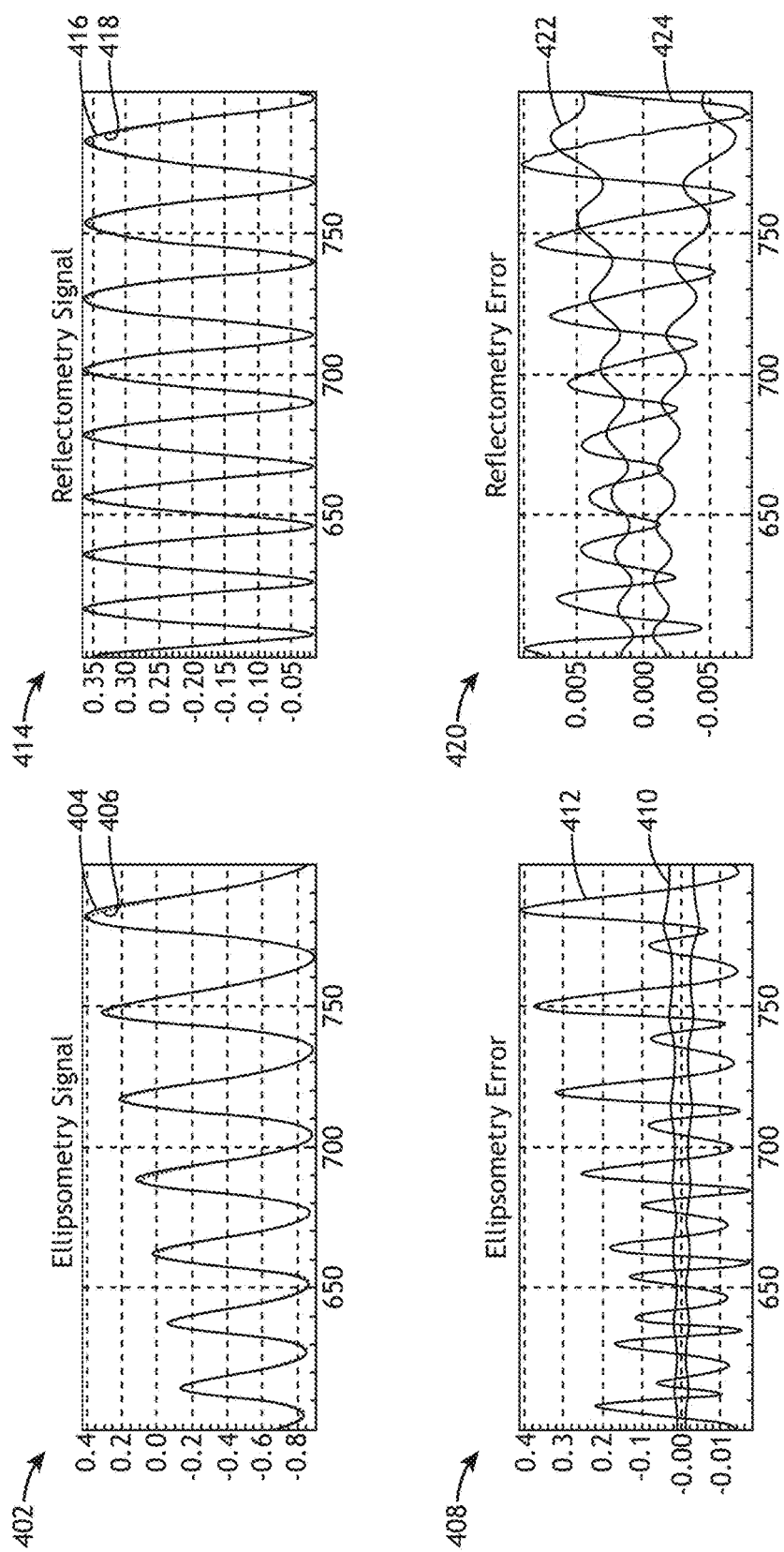
FIG. 4 includes plots comparing simulated signals with regression fits using an effective medium model of a multilayer film stack with a single zone of 96 pairs of repeating layers formed from repeating oxide and nitride layers with nominal thicknesses of 300 and 300 Angstroms, respectively, in accordance with one or more embodiments of the present disclosure.
Figure 5:
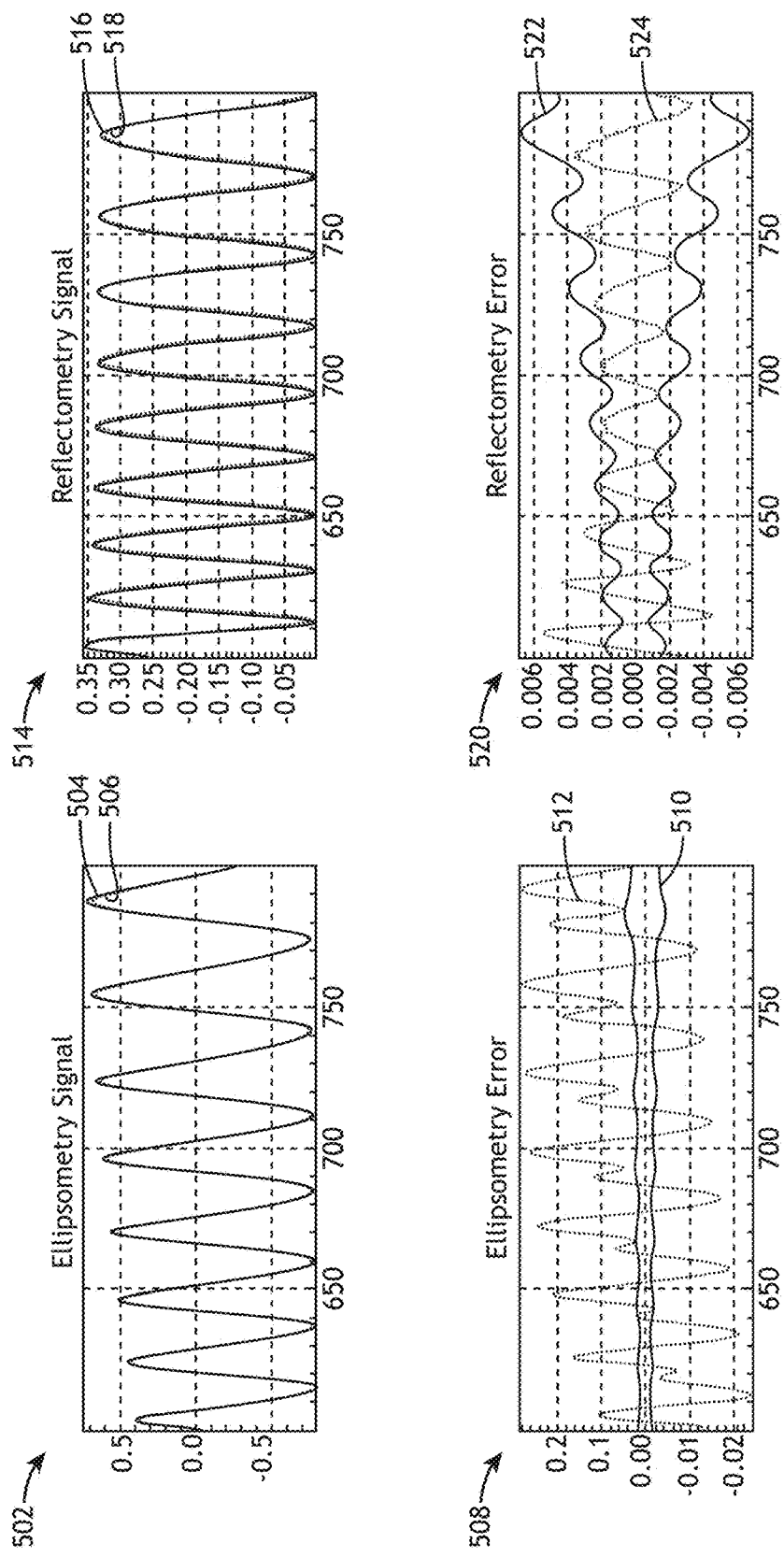
FIG. 5 includes plots comparing simulated signals with regression fits using an effective medium model of a multilayer film stack with a single zone of 96 pairs of repeating layers formed from repeating oxide and nitride layers with nominal thicknesses of 200 and 400 Angstroms, respectively, in accordance with one or more embodiments of the present disclosure.
Figure 6:
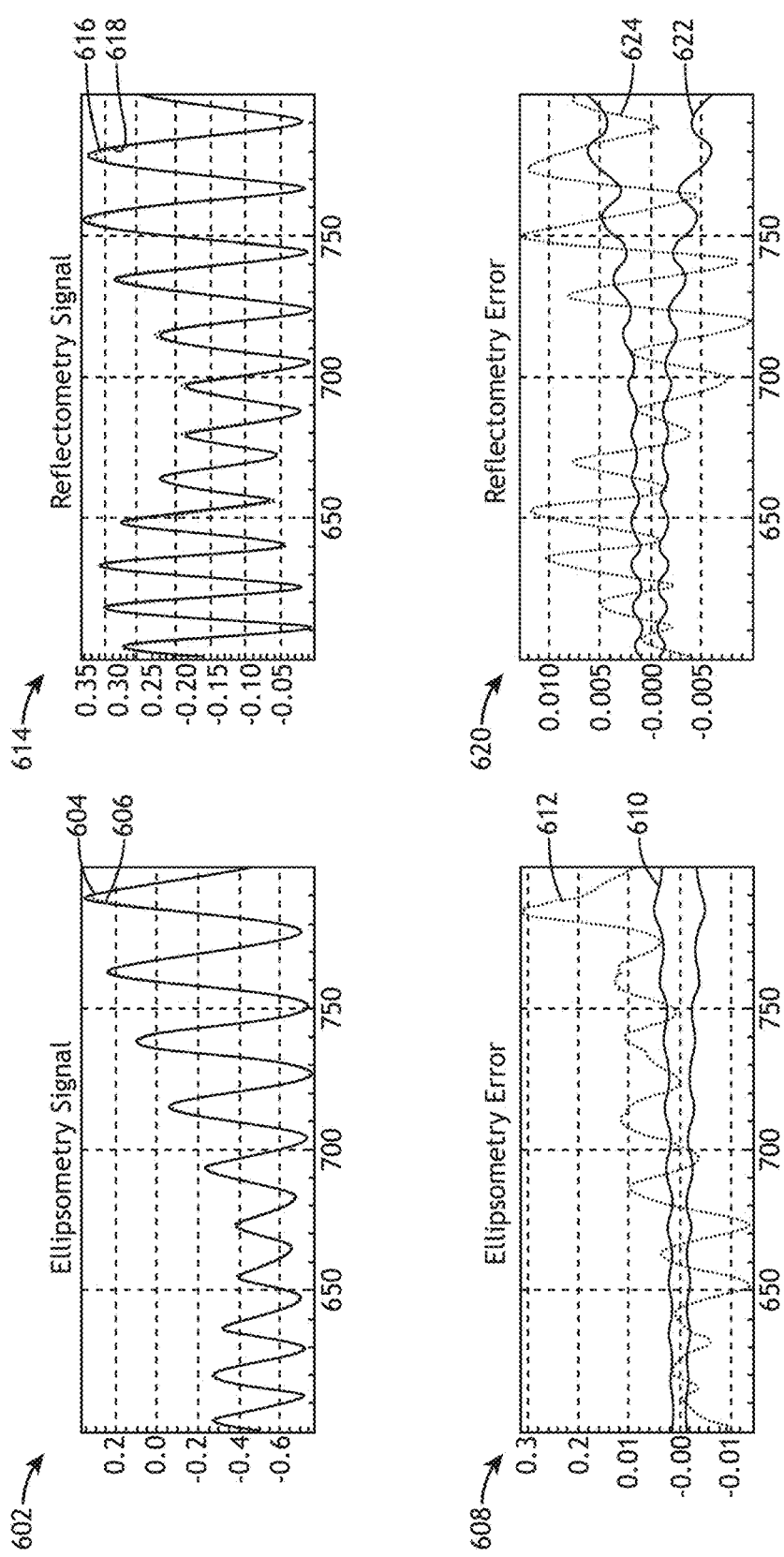
FIG. 6 includes plots comparing simulated signals with regression fits using an effective medium model of multilayer film stack including a single zone of 96 pairs of repeating layers formed from repeating oxide and nitride layers with nominal thicknesses of 300 and 300 Angstroms, respectively, along with a 10,000 Angstrom-thick top oxide layer and a 10,000 Angstrom-thick bottom layer, in accordance with one or more embodiments of the present disclosure.

Referring now to FIGS. 4 through 6, applications of the method 200 are described, in accordance with one or more embodiments of the present disclosure. In one embodiment, a multilayer film stack 104 includes a single zone of 96 pairs of alternating oxide and nitride repeating film layers 302 layers on a silicon substrate 322 as depicted in FIGS. 3A and 3B. For example, the first composition 304 is an oxide material and the second composition 306 is a nitride material.

In the examples illustrated in FIGS. 4 through 6, the multilayer film stack 104 is modeled as a uniaxial material in which the permittivity was modeled according to Eq. (2). Further, the volume fractions of the oxide and nitride layers were constrained as:

$$f_{v,t}(\text{nitride})=1-f_{v,t}(\text{oxide}) \text{ and } f_{v,z}(\text{nitride})=1-f_{v,z}(\text{oxide}). \quad (4)$$

In this regard, the volume fractions for the oxide ($f_{v,t}$(oxide) and $f_{v,z}$(oxide)), along with the zone thickness (e.g., zone thickness 308) were floated as unknown variables in a regression analysis in step 206 of the method 200. The average thickness values of the oxide and nitride layers was then determined based on the volume fractions along the Z direction based on Eq. (1).

FIG. 4 includes plots comparing simulated signals with regression fits using an effective medium model of a multilayer film stack 104 with a single zone of 96 pairs of repeating layers 302 formed from repeating oxide and nitride layers with nominal thicknesses of 300 and 300 Angstroms, respectively, in accordance with one or more embodiments of the present disclosure. In this regard, the multilayer film stack 104 is designed according to FIG. 3A with a nominal zone thickness 308 of 57,600 Angstroms. Plot 402 includes a simulated ellipsometry signal 404 associated with spectroscopic ellipsometry measurements (e.g., associated with in step 202) and a regression fit signal 406 (e.g., associated with step 206) over a wavelength range of 600 nm to 800 nm based on the effective medium model of the multilayer film stack 104. Plot 408 includes a corresponding ellipsometry error signal 410 and a 1σ noise model signal 412. Plot 414 includes a simulated reflectometry signal 416 associated with spectroscopic reflectometry measurements (e.g., in step 202) and a regression fit signal 418 over a range of 600 nm to 800 nm based on the effective medium model of the multilayer film stack 104. Plot 420 includes a corresponding reflectometry error signal 422 and a 1σ noise model signal 424.

In the EMA model (e.g., associated with step 204), the permittivity values of the oxide and the nitride materials were modeled based on wavelength-independent refractive index values of 1.5 and 2.0, respectively. The regression analysis of step 206 then determined the volume fraction along the Z direction, $f_z$(oxide), to be 0.502 and the zone thickness 308 to be 57,608 Angstroms. The average thicknesses of the oxide and the nitride layers were determined to be 301.25 Angstroms and 298.85 Angstroms, respectively, based on these values in step 208. The corresponding error associated with thickness determination using method 200 was 0.4% for the oxide layers and −0.4% for the nitride layers, respectively.

FIG. 5 includes plots comparing simulated signals with regression fits using an effective medium model of a multilayer film stack 104 with a single zone of 96 pairs of repeating layers formed from repeating oxide and nitride layers with nominal thicknesses of 200 and 400 Angstroms, respectively, in accordance with one or more embodiments of the present disclosure. In this regard, the multilayer film stack 104 is designed according to FIG. 3A with a nominal zone thickness 308 of 57,600 Angstroms. Plot 502 includes a simulated ellipsometry signal 504 associated with spectroscopic ellipsometry measurements (e.g., associated with in step 202) and a regression fit signal 506 (e.g., associated with step 206) over a wavelength range of 600 nm to 800 nm based on the effective medium model of the multilayer film stack 104. Plot 508 includes a corresponding ellipsometry error signal 510 and a 1σ noise model signal 512. Plot 514 includes a simulated reflectometry signal 516 associated with spectroscopic reflectometry measurements (e.g., in step 202) and a regression fit signal 518 over a range of 600 nm to 800 nm based on the effective medium model of the multilayer film stack 104. Plot 520 includes a corresponding reflectometry error signal 522 and a 1σ noise model signal 524.

In the EMA model (e.g., associated with step 204), the permittivity values of the oxide and the nitride materials were modeled based on wavelength-dependent complex analytic dispersion models. The regression analysis of step 206 then determined the volume fraction along the Z direction, $f_Z$(oxide), to be 0.331 and the zone thickness 308 to be 57,543 Angstroms. The average thicknesses of the oxide and the nitride layers were determined to be 198.56 Angstroms and 400.85 Angstroms, respectively, based on these values in step 208. The corresponding error associated with thickness determination using method 200 was −0.7% for the oxide layers and 0.2% for the nitride layers, respectively.

FIG. 6 includes plots comparing simulated signals with regression fits using an effective medium model of multilayer film stack 104 including a single zone of 96 pairs of repeating layers formed from repeating oxide and nitride layers with nominal thicknesses of 300 and 300 Angstroms, respectively, along with a 10,000 Angstrom-thick top oxide layer and a 10,000 Angstrom-thick bottom layer, in accordance with one or more embodiments of the present disclosure. In this regard, the multilayer film stack 104 is designed according to FIG. 3B with a nominal zone thickness 308 of 57,600 Angstroms. Plot 602 includes a simulated ellipsometry signal 604 associated with spectroscopic ellipsometry measurements (e.g., associated with in step 202) and a regression fit signal 606 (e.g., associated with step 206) over a wavelength range of 600 nm to 800 nm based on the effective medium model of the multilayer film stack 104. Plot 608 includes a corresponding ellipsometry error signal 610 and a 1σ noise model signal 612. Plot 614 includes a simulated reflectometry signal 616 associated with spectroscopic reflectometry measurements (e.g., in step 202) and a regression fit signal 618 over a range of 600 nm to 800 nm based on the effective medium model of the multilayer film stack 104. Plot 620 includes a corresponding reflectometry error signal 622 and a 1σ noise model signal 624.

In the EMA model (e.g., associated with step 204), the permittivity values of the oxide and the nitride materials were modeled based on wavelength-dependent complex analytic dispersion models. In the regression analysis of step 206, the zone thickness 308, the thickness of the top layer 314, the thickness of the bottom layer 316, and the volume fractions of the oxide material along the Z and X-Y directions were floated as unknown variables. The resulting analysis provided an oxide volume fraction along the Z direction, $f_Z$(oxide), to be 0.331 and the zone thickness 308 to be 57,543 Angstroms. The average thicknesses of the oxide and the nitride layers were then determined to be 297.68 Angstroms and 299.68 Angstroms, respectively, based on these values in step 208. The corresponding error associated with thickness determination using method 200 was −0.8% for the oxide layers and −0.1% for the nitride layers, respectively. Further, top layer thickness was determined to be 10,136 Angstroms with an error of 1.36% and the bottom layer thickness was determined to be 10,132 Angstroms with an error of 1.32%.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected" or "coupled" to each other to achieve the desired functionality, and any two components capable of being so associated can also be viewed as being "couplable" to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction, and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A metrology system comprising:
a controller communicatively coupled to a detector configured to generate a detection signal based on reflection of an illumination beam from a multilayer film stack, wherein the multilayer film stack includes one or more zones with two or more material compositions disposed in a repeating pattern, wherein a number of layers of each material composition within the one or more zones is known, the controller including one or more processors configured to execute program instructions causing the one or more processors to:
model reflection of the illumination beam by the multilayer film stack by modeling the one or more zones of repeating layers of the multilayer film stack as thick films having zone thicknesses and effective permittivity values using an effective medium model, wherein the effective medium model relates the effective permittivity values of the one or more zones to permittivity values of the two or more material compositions and volume fractions of the two or more material compositions within the one or more zones;
determine values of the zone thicknesses and the volume fractions using a regression of the detection signal based on the effective medium model; and
determine average thickness values of the two or more material compositions within the one or more zones based on the number of films having each of the two or more material compositions, the zone thicknesses, the volume fractions, and the effective permittivity values.

2. The metrology system of claim 1, wherein the multilayer film stack further includes one or more non-repeating layers, wherein the one or more processors are further configured to execute program instructions causing the one or more processors to:
determine values of the thicknesses of the one or more non-repeating layers using the regression of the detection signal based on the effective medium model.

3. The metrology system of claim 2, wherein the one or more non-repeating layers comprise:
at least one of a top layer, a bottom layer, or an intermediate layer between two zones of repeating layers.

4. The metrology system of claim 1, wherein the effective medium approximation model comprises:
a uniaxial film model.

5. The metrology system of claim 4, wherein the volume fractions comprise:
a first set of volume fractions associated with ordinary dispersion and a second set of volume fractions associated with extraordinary dispersion.

6. The metrology system of claim 1, wherein the detection signal comprises:
at least one of a reflectometry, scatterometry, or ellipsometry detection signal.

7. The metrology system of claim 1, wherein an illumination source of the illumination beam comprises:
a narrowband illumination source.

8. The metrology system of claim 1, wherein an illumination source of the illumination beam comprises:
a broadband illumination source.

9. The metrology system of claim 1, wherein the detector comprises:
a spectroscopic detector, wherein the detection signal comprises:
at least one of a spectroscopic reflectometry, or a spectroscopic ellipsometry detection signal.

10. The metrology system of claim 1, wherein wavelengths of the illumination beam are at least an order of magnitude higher than thicknesses of the two or more repeating compositions.

11. The metrology system of claim 1, wherein wavelengths of the illumination beam include at least one of ultraviolet, visible, or infrared wavelengths.

12. A metrology system comprising:
an illumination source configured to generate an illumination beam;
one or more illumination optical elements configured to direct the illumination beam to a multilayer film stack, wherein the multilayer film stack includes one or more zones with two or more material compositions disposed in a repeating pattern, wherein a number of layers of each material composition within the one or more zones is known;
one or more collection optical elements configured to capture reflected light from the multilayer film stack in response to the illumination beam;
a detector to generate a detection signal based on the light captured by the one or more collection optical elements; and
a controller communicatively coupled to the detector, the controller including one or more processors configured to execute program instructions causing the one or more processors to:
model reflection of the illumination beam by the multilayer film stack by modeling the one or more zones of repeating layers of the multilayer film stack as thick films having zone thicknesses and effective permittivity values using an effective medium model, wherein the effective medium model relates the effective permittivity values of the one or more zones to permittivity values of the two or more material compositions and volume fractions of the two or more material compositions within the one or more zones;
determining values of the zone thicknesses and the volume fractions using a regression of the detection signal based on the effective medium model; and
determine average thickness values of the two or more material compositions within the one or more zones based on the number of films having each of the two or more material compositions, the zone thicknesses, the volume fractions, and the effective permittivity values.

13. The metrology system of claim 12, wherein the multilayer film stack further includes one or more non-repeating layers, wherein the one or more processors are further configured to execute program instructions causing the one or more processors to:
determine values of the thicknesses of the one or more non-repeating layers using the regression of the detection signal based on the effective medium model.

14. The metrology system of claim 13, wherein the one or more non-repeating layers comprise:
at least one of a top layer, a bottom layer, or an intermediate layer between two zones of repeating layers.

15. The metrology system of claim 12, wherein the effective medium approximation model comprises:
a uniaxial film model.

16. The metrology system of claim 15, wherein the volume fractions comprise:
a first set of volume fractions associated with ordinary dispersion and a second set of volume fractions associated with extraordinary dispersion.

17. The metrology system of claim 12, wherein the detection signal comprises:
at least one of a reflectometry, scatterometry, or ellipsometry detection signal.

18. The metrology system of claim 12, wherein the illumination source comprises:
a narrowband illumination source.

19. The metrology system of claim 12, wherein the illumination source comprises:
a broadband illumination source.

20. The metrology system of claim 12, wherein the detector comprises:
a spectroscopic detector, wherein the detection signal comprises:
at least one of a spectroscopic reflectometry, or a spectroscopic ellipsometry detection signal.

21. The metrology system of claim 12, wherein wavelengths of the illumination beam are at least an order of magnitude higher than thicknesses of the two or more repeating compositions.

22. The metrology system of claim 12, wherein wavelengths of the illumination beam include at least one of ultraviolet, visible, or infrared wavelengths.

23. A method for determining layer thicknesses of a multilayer film comprising:
measuring light reflected from a multilayer film stack to generate a detection signal, wherein the multilayer film stack includes one or more zones with two or more material compositions disposed in a repeating pattern, wherein a number of layers of each material composition within the one or more zones is known;
modeling reflection of the light by the multilayer film stack by modeling the one or more zones of repeating layers of the multilayer film stack as thick films having zone thicknesses and effective permittivity values using an effective medium model, wherein the effective medium model relates the effective permittivity values of the one or more zones to permittivity values of the two or more material compositions and volume fractions of the two or more material compositions within the one or more zones;

determining values of the zone thicknesses and the volume fractions using a regression of the detection signal based on the effective medium model; and determining average thickness values of the two or more material compositions within the one or more zones based on the number of films having each of the two or more material compositions, the zone thicknesses, the volume fractions, and the effective permittivity values.

* * * * *